United States Patent
Hoegele

(10) Patent No.: US 9,046,688 B2
(45) Date of Patent: Jun. 2, 2015

(54) SURGICAL MICROSCOPE WITH ENLARGED WORKING DISTANCE

(71) Applicant: Carl Zeiss Meditec AG, Jena (DE)

(72) Inventor: Artur Hoegele, Oberkochen, DE (US)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 14/272,866

(22) Filed: May 8, 2014

(65) Prior Publication Data

US 2014/0340500 A1 Nov. 20, 2014

(30) Foreign Application Priority Data

May 10, 2013 (DE) .......................... 10 2013 008 090

(51) Int. Cl.
| | | |
|---|---|---|
| H04N 9/47 | (2006.01) | |
| H04N 7/18 | (2006.01) | |
| G01B 11/00 | (2006.01) | |
| G02B 21/00 | (2006.01) | |
| G02B 15/02 | (2006.01) | |
| G02B 21/02 | (2006.01) | |
| G02B 21/22 | (2006.01) | |
| A61B 19/00 | (2006.01) | |

(52) U.S. Cl.
CPC ................ *G02B 21/02* (2013.01); *G02B 21/22* (2013.01); *G02B 21/0012* (2013.01); *A61B 19/5223* (2013.01)

(58) Field of Classification Search
CPC ..... G02B 21/02; G02B 21/0012; G02B 21/22
USPC .......................................................... 348/79
See application file for complete search history.

(56) References Cited

U.S. PATENT DOCUMENTS

| | | | | |
|---|---|---|---|---|
| 4,110,005 | A * | 8/1978 | Bohm et al. ................... | 359/673 |
| 4,299,453 | A | 11/1981 | Momiyama et al. | |
| 5,424,838 | A * | 6/1995 | Siu ................................ | 356/394 |
| 2006/0114554 | A1 * | 6/2006 | Suzuki et al. ................. | 359/380 |

FOREIGN PATENT DOCUMENTS

| | | |
|---|---|---|
| DE | 29 27 478 C2 | 1/1980 |
| DE | 195 23 712 C2 | 1/1996 |
| DE | 10 2005 050 171 A1 | 4/2007 |

OTHER PUBLICATIONS

Decision to Grant in corresponding German Patent Application No. 10 2013 008 090.8, dated Mar. 19, 2014.
German Office Action in corresponding German Patent Application No. 10 2013 008 090.8 dated Jul. 17, 2013.
Decision to Grant in corresponding German Patent Application No. 10 2013 008 090.8 dated Jul. 17, 2013.

* cited by examiner

*Primary Examiner* — Hee-Yong Kim
(74) *Attorney, Agent, or Firm* — Patent Portfolio Builders PLLC

(57) ABSTRACT

A surgical microscope 1 comprises an imaging system 2 providing a magnified multidimensional image of an object 3 disposable in a focal plane 4 of the imaging system 2 along at least one optical imaging path 2a, 2b. The imaging system 2 comprises an objective 5 having at least two lens groups 6, 7, through which the at least one optical imaging path 2a, 2b passes consecutively, and which define the focal plane 4 of the imaging system 2. At least one lens group 6 of the objective is moveable along its optical axis relative to the at least one other lens group 7 of the objective. The objective's first lens group 6 located directly adjacent to the focal plane 4 along the at least one optical imaging path 2a, 2b consists of at least three optical lenses 61, 62, 63 and has altogether a negative optical power.

21 Claims, 3 Drawing Sheets

IMAGE

OBJECT

SURGICAL MICROSCOPE WITH ENLARGED WORKING DISTANCE

CROSS-REFERENCES TO RELATED APPLICATIONS

The present application claims priority of Patent Application No. 10 2013 008 090.8, filed May 10, 2013 in Germany, the entire contents of which are incorporated by reference herein.

FIELD OF THE INVENTION

The present invention relates to a surgical microscope (also referred to as operating microscope) adapted for enabling a variation of its working distance to a wide extent.

BACKGROUND

Surgical microscopes are optical reflected-light microscopes designed for use in medical surgery and providing a magnification typically in the range from 5×-30×. Compared to other optical reflected-light microscopes, surgical microscopes use an objective having an enlarged focal distance of typically between 175 mm and 550 mm and a correspondingly large working distance (distance between the lens vertex of the objective lens of a surgical microscope located closest to an object to be imaged and the object) of typically between 200 mm and 500 mm. For providing a user with a three-dimensional impression of an object to be imaged, surgical microscopes are often configured as stereoscopic microscopes (also referred to as stereo microscopes) providing a pair of optical imaging paths for the eyes of a user, with the optical imaging paths intersecting close to a focal plane of the surgical microscope at a stereoscopic angle of typically between 3° and 14°. The field of view of surgical microscopes, i.e. the area located in the focal plane that can be imaged at a given time by the at least one optical imaging path onto the retina of a user, is typically larger than 1 mm². The field of view of a surgical microscope thus not only comprises a single image point as is the case with scanning microscopes; rather a multi-dimensional (two or three-dimensional) imaging of the object observed takes place at any point in time. Surgical microscopes are often equipped with a zoom system or a magnification changer for enabling a change in magnification, and a focusing system for changing the working distance. Regular fields of application are surgery and microsurgery.

In surgical microscopes, the image of an object imaged with the operation microscope is alternatively provided to a user by an eyepiece (or in stereoscopic surgical microscopes by a pair of eyepieces), or the image is converted in electrical signals using an image converter (or in stereoscopic surgical microscopes using a stereo image converter or a pair of image converters), and is displayed to the user in addition or alternatively to the eyepieces by at least one of a monitor and a head-mounted display.

Surgical microscopes are often supported by stands mounted to a floor or a ceiling of a treatment room or can be positioned freely across the floor of the treatment room. The stand may be adjustable manually by use of motors, and allows desired positioning and orientation of the surgical microscope above the object to be imaged.

In addition to surgical microscopes, also monoscopical overview cameras having no or only little magnification at a working distance of typically 1,000 mm are frequently used during medical surgery. The simultaneous provision of an overview camera in addition to a surgical microscope increases complexity, since there are two different tools to be handled, and increases cost, since two different tools need to be procured and maintained.

Despite the larger working distance as compared to conventional reflected-light microscopes, the range of working distances achieved with common surgical microscopes is unsatisfactory.

SUMMARY OF THE INVENTION

Embodiments are therefore directed to a surgical microscope enabling a variation of its working distance to a wide extent, and in particular a larger working distance as compared to common surgical microscopes.

Embodiments of a surgical microscope comprise an imaging system that includes an objective (may also be referred to as objective system) capable of generating a magnified multidimensional (in particular two or three-dimensional) image of a (normally three-dimensional) object located in the focal plane of the imaging system along at least one optical path. If no object is located in the focal plane, the focal plane itself is imaged.

The objective comprises at least two lens groups that are one after another passed through by the at least one optical imaging path, and which define the focal plane of the imaging system.

According to an embodiment, the objective comprises just two lens groups.

According to an embodiment, a lens group is to be understood as a subset of the optical lenses disposed in the surgical microscope characterized by meeting all of the following criteria:

- the same at least one optical imaging path consecutively passes through the optical lenses of the subset. Along the same at least one optical imaging path, no optical lenses belonging to a different lens group or to no lens group are thus present between the optical lenses of a lens group.
- the optical lenses of the subset are fixed with respect to each other, i.e. the distances between any adjacent optical lenses of all optical lenses of a lens group are non-varying and thus constant. This does, however, not preclude a common movement of all optical lenses of the lens group relative to an optical lens or lens group not being part of this lens group (or being different from the lens group considered).
- no imaging of the focal plane to infinity takes place between optical lenses of the subset, i.e., a lens group may not comprise an afocal interface. However, where applicable the lens group may begin after an afocal interface and/or end before an afocal interface.

At least one lens group of the objective is moveable along its optical axis relative to at least one other lens group of the objective. The first lens group of the objective, which is along the at least one imaging path located directly adjacent to the focal plane, consists altogether of at least three optical lenses and has a negative optical power (reciprocal of the focal length).

The term "directly adjacent" does hereby explicitly not exclude that additional optical elements having no or only very little optical power are disposed between the focal plane and the objective. Optical elements having only very little optical power are understood as optical elements having an optical power the absolute value of which does not exceed 10%, and in particular does not exceed 5%, and further in particular does not exceed 3% of the overall optical power of the surgical microscope. Optical elements having no or only very little optical power like e.g. cover disks or flat filters are therefore not to be considered when verifying the "directly adjacent" criterion. This means that no further optical lenses or lens groups are disposed between the first lens group and the focal plane.

The construction of the objective with two lens groups, with one of these lens groups consisting of at least three lenses and having a negative optical power altogether, enables to vary the working distance in a range that goes beyond the range typical for surgical microscopes.

According to an embodiment, the objective has an adjustable focal length of between 150 mm and infinity, and in particular of between 200 mm and 1,200 mm, and further in particular of between 300 mm and 600 mm.

According to an embodiment, the objective has an adjustable working distance of between 200 mm and 5,000 mm.

In addition to the objective, the imaging system may have further optical lenses that are one after another passed through by the at least one optical imaging path. The objective is disposed closest to the object imaged along the at least one optical imaging path. This means that the objective is disposed between other optical lenses of the imaging system and the focal plane. The optical lenses, including the optical lenses of the objective, may be simple lens elements and/or cemented elements. The imaging system may further comprise one or more optical mirrors consecutively folding the optical imaging path.

According to an embodiment and with regard to absolute values, the focal length of the objective's first lens group does not exceed 35%, and in particular not 25%, and further in particular not 20% of the minimum overall focal length of the objective. According to an embodiment, the focal length of the objective's first lens group is at the same time, with respect to absolute values, at least 10%, and in particular at least 15% of the minimum overall focal length of the objective.

The first lens group of the objective accordingly has, with respect to the absolute value, an unusual high proportion on the optical power as compared to common objectives for surgical microscopes, particularly since the first lens group has an altogether negative optical power.

According to an embodiment, each optical lens of the first lens group of the objective has a focal length, which absolute value is between 80% and 300%, and in particular between 95% and 200% of the absolute value of the focal length of the first lens group of the objective.

Within the first lens group, the optical power is thus fairly equally distributed across the optical lenses of the first lens group.

According to an embodiment, the absolute value of the ratio of the focal length of the first lens group of the objective to the focal length of the second lens group of the objective is between 0.75 and 1.00, and in particular between 0.80 and 0.90, and further in particular between 0.82 and 0.88.

According to an embodiment, the first lens group of the objective consists of exactly three optical lenses, whereby in particular two of the optical lenses are joined together permanently by bonding to form a cemented element, and whereby the third optical lens forms a lens element separate from the cemented element. The permanently joined lenses are hereby made from materials of different refractive index. The cemented element may then be disposed either between the focal plane and the separate lens element or the separate lens element may be disposed between focal plane and the cemented element.

According to an embodiment, the optical power of the second lens group of the objective that is located along the at least one optical imaging path directly adjacent to the first lens group is altogether positive.

According to an embodiment, the second lens group of the objective consists of just three optical lenses, whereby in particular two of the optical lenses are joined together permanently by bonding to form a cemented element, and whereby the third optical lens forms a lens element separate from the cemented element. The permanently joined lenses are hereby made from materials of different refractive index. The cemented element may then be disposed either between the focal plane and the separate lens element or the separate lens element may be disposed between the focal plane and the cemented element.

According to an embodiment, the same at least one optical imaging path consecutively passes through the optical lenses of each lens group, while the optical lenses of each lens group are stationary relative to other lenses of the same lens group.

According to an embodiment, within a lens group, no imaging of the focal plane to infinity takes place.

According to an embodiment, the objective as a whole causes an imaging of an object disposable in the focal plane of the imaging system to infinity. This enables a modular structure of the surgical microscope.

According to an embodiment, no imaging of an object disposable in the focal plane to infinity is effected within the objective.

According to an embodiment, the imaging system provides at least one pair of optical imaging paths intersecting in the focal plane of the imaging system under a stereoscopic angle $\alpha$ of between 3° and 14° with each imaging an object disposed in the focal plane of the imaging system into a magnified multidimensional (and in particular two-dimensional) image of the object. Altogether, this enables a provision of a three-dimensional image of the object. Hereby, the at least one pair of optical imaging paths collectively passes through the optical lenses of the objective. The optical imaging paths of the at least one pair of optical imaging paths may overlap each other in part inside the optical lenses of the objective or may not overlap each other. In particular, principal rays of the optical imaging paths may in pairs be equally offset to the optical axes of the lenses of the objective through which they collectively pass.

According to an embodiment, the surgical microscope further comprises a zoom system having a plurality of optical lenses, whereby only one optical imaging path of the at least one pair of optical imaging paths passes through the optical lenses of the zoom system consecutively.

According to an embodiment, the surgical microscope further comprises a variable aperture stop for each optical imaging path of the at least one pair of optical imaging paths.

According to an embodiment, the surgical microscope further comprises at least one imaging sensor disposed in an image plane of the imaging system and outputting image data representing the image of the object generated by the imaging system. The image sensor may be provided in addition or alternatively to eyepieces. A surgical microscope comprising no eyepieces is referred to as a "digital surgical microscope"; in this case, the arrangement and position of the surgical microscope is completely independent from the arrangement and position of the image display during imaging.

The image data output from the at least one image sensor may be provided in form of an electrical (and where required digital) signal, which enables a reconstruction—in particular one ensuring color fidelity—of the object image generated by the imaging system. This means that the signal output from the imaging sensor contains an information content corresponding to the information content of the image of the object generated by the imaging system to an extend enabling a reproduction of the image on a display based on the signal. The at least one image sensor may for instance be a silicon sensor, and in particular a CCD-sensor (optionally with a preceding filter wheel or color sensitive sensors instead), or an active-pixel sensor based on CMOS technology. According to an embodiment, an area of the image sensor sensitive to light has an area of at least 100×100 picture elements, and in particular of at least 320×240 picture elements.

When using an image sensor, the surgical microscope may further comprise a display (for example a monitor, a digital projector, or a head-mounted display), for displaying the image obtained from the image sensor.

According to an embodiment, the surgical microscope further comprises a controller configured to automatically control the objective of the imaging system such that the imaged object is continuously maintained in the focal plane of the imaging system. This results in the imaging system producing a sharp image of the object imaged even during a change in magnification. A respective functionality is also referred to as autofocus.

According to an embodiment, the surgical microscope further comprises a radiation source providing an illumination beam path passing through the lens groups of the objective along the optical axes of the lens groups.

According to an embodiment, a stand supports the surgical microscope. The stand can be fixedly mounted to a wall, a floor, or a ceiling or be for instance moveable by rolls.

According to an embodiment, the surgical microscope is a digital surgical microscope which imaging system does not comprise any eyepieces.

It is noted that the above embodiments may be combined in any possible manner.

The terms "including", "comprising", "containing", "having" and "with", as well as grammatical modifications thereof used in this specification or the claims for listing features, are generally to be considered to specify a non-exhaustive listing of features like for instance method steps, components, ranges, dimensions or the like, and do by no means preclude the presence or addition of one or more other features or groups of other or additional features.

BRIEF DESCRIPTION OF THE DRAWINGS

The forgoing as well as other advantageous features of the disclosure will be more apparent from the following detailed description of exemplary embodiments together with the claims and the Figures. In the Figures, like or similar elements are indicated by like or similar reference signs. It is noted that the invention is not limited to the embodiments of the exemplary embodiments described, but is defined by the scope of the enclosed claims, and that not all possible embodiments necessarily exhibit each and every, or any, of the advantages identified herein. In particular, embodiments according to the invention may implement individual features in a different number and combination than the examples instanced below. In the following explanation of an exemplary embodiment of the invention, it is referred to the enclosed Figures, of which

Figure 1:
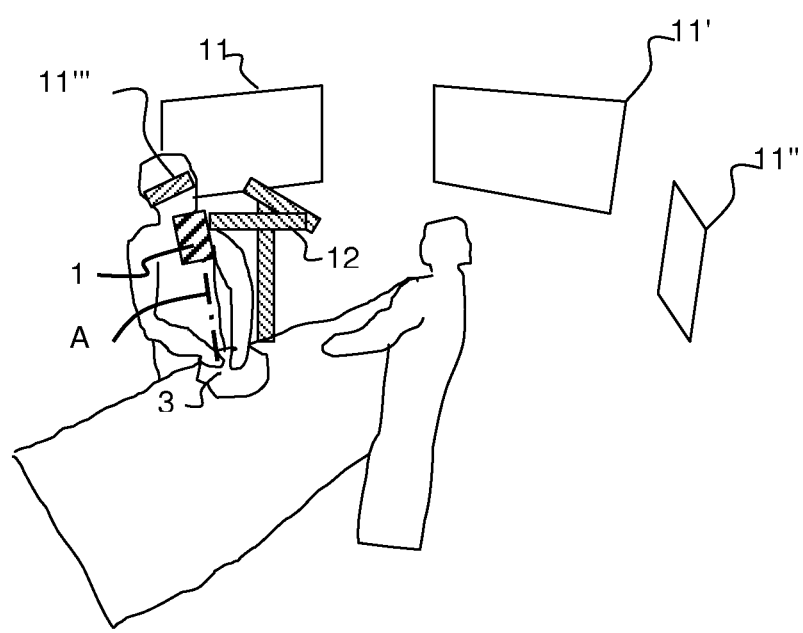
FIG. 1 shows a schematic representation of an application of a surgical microscope according to an embodiment of the invention.

In the exemplary embodiments described below, components that are alike in function and structure are indicated as far as possible by alike reference numerals. Therefore, to understand the features of the individual components of a specific embodiment, the descriptions of other embodiments and of the summary of the disclosure should be referred to.

DETAILED DESCRIPTION OF EXEMPLARY EMBODIMENTS

With reference to FIG. 1, a schematic representation of an exemplary use of a surgical microscope 1 according to an embodiment of the invention in a surgical procedure is shown.

The surgical microscope 1 is supported by a floor stand 12 moveable on rollers (not shown), and by using the stand, a user can move it manually such that an optical axis A of an objective (shown in FIG. 2) is directed onto an operation area 3 to be imaged. The magnified image of the operation area 3 generated by the surgical microscope 1 is output via lines (not shown) and three monitors 11, 11', and 11'', as well as to a head-mounted display 11''' of a user via a radio interface.

Figure 2:
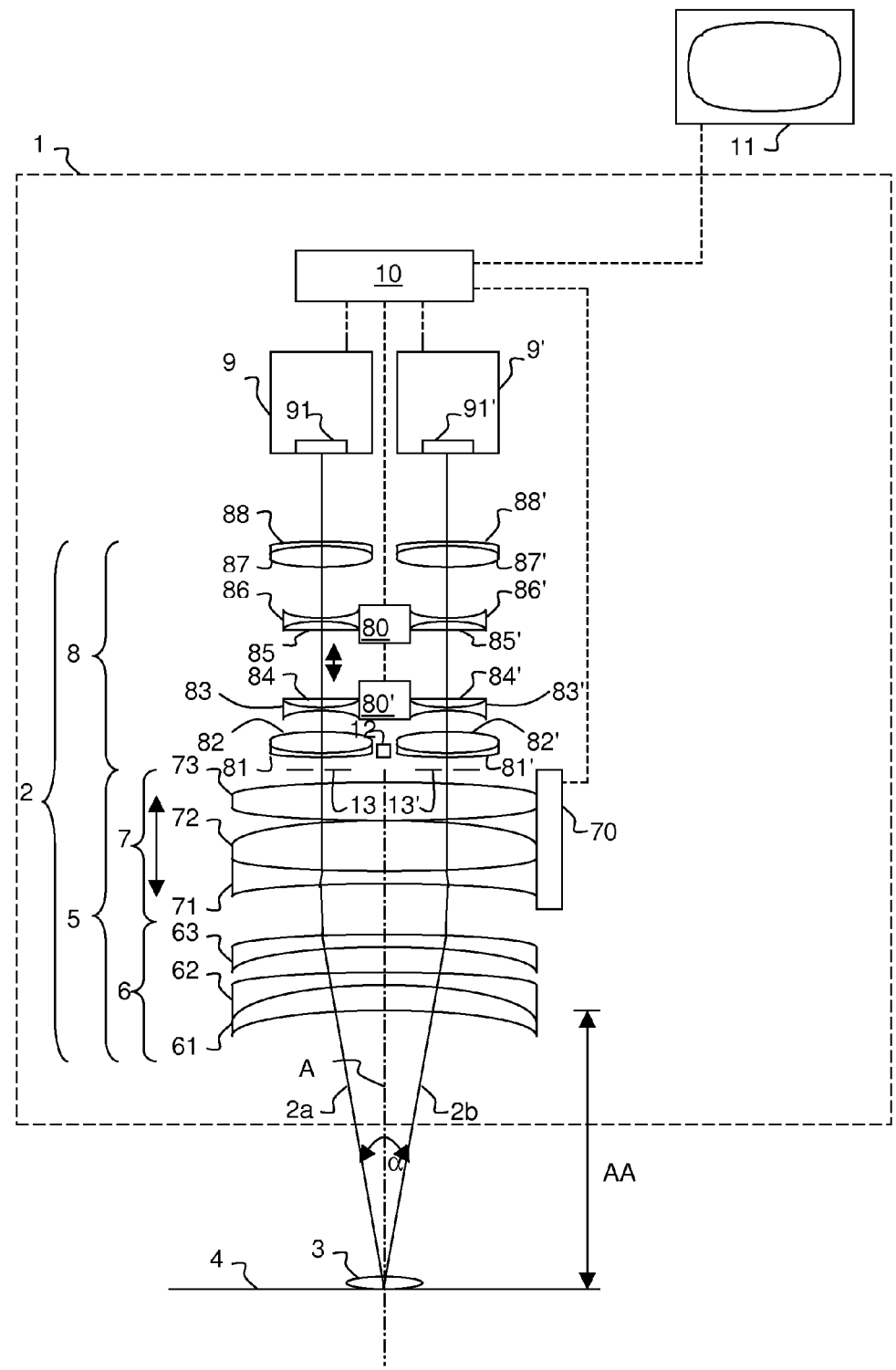
FIG. 2 shows a schematic cross sectional view of the construction of the surgical microscope of FIG. 1.

As schematically shown in FIG. 2, the surgical microscope 1 of FIG. 1 is a stereoscopic microscope having an imaging system 2 providing two optical imaging paths 2a, 2b intersecting in a focal plane 4 of the imaging system 2 of the surgical microscope 1 at a stereoscopic angle $\alpha$. The value of the stereoscopic angle $\alpha$ depends on the respective working distance chosen and is between 6° and 10° for the digital surgical microscope shown.

It is noted that the paths of the principal rays of the optical imaging paths 2a, 2b are shown in FIG. 2 only schematically. Therefore, FIG. 2 shows the refractive effect of the lenses therefore only imperfectly.

In the embodiment shown, the imaging system 2 is comprised of a two-part objective 5 and a four-part zoom system 8. It is noted that the present invention is not limited to two-part objectives or four-part zoom systems, but may generally also use multi-part systems.

The objective 5 comprises two lens groups 6, 7 consecutively passed through by both stereoscopic optical imaging paths 2a, 2b together, with the two lens groups imaging the whole operation area 3 to infinity. Accordingly, an afocal interface is provided between the objective 5 and the zoom system 8.

The lens group 6 located closest to the operating area 3 to be imaged along the stereoscopic optical imaging paths 2a, 2b has an altogether negative optical power and consists of three optical lenses 61, 62, 63 disposed with a fixed distance relative to each other. The two optical lenses 61, 62 of the first lens group 6 that are closest to the operation area 3 under observation are made from materials with different refractive indices and are permanently bonded face-to-face to each other for forming a cemented element. The remaining third lens 63 of the first lens group 6 is a simple lens element located at a fixed distance from the cemented element of the first lens group 6. In the embodiment shown, the optical lens 61 has a focal length which absolute value is 146%, the optical lens 62 has a focal length which absolute value is 98%, and the optical lens 63 has a focal length which absolute value is 157% of the overall focal length of the first lens group 6 of the objective 5.

It is noted that the present invention is not limited to an objective having a first lens group where the cemented element is located between the ordinary lens element and the focal plane. For example, the single lens element may alternatively also be located between the cemented element and the focal plane.

The other second lens group 7 has altogether a positive optical power and consists also of three optical lenses 71, 72, 73 arranged with fixed distances relative to each other. The two optical lenses 71, 72 of the second lens group 7 that are closest to the operation area 3 under observation are made from materials with different refractive indices and are permanently bonded face-to-face to each other for forming a cemented element. The remaining third lens 73 of the second lens group 7 is a ordinary lens element located at a fixed distance from the cemented element of the second lens group 7.

In the embodiment shown, the optical axes A of all optical lenses 61, 62, 63, 71, 72, 73 of the first and second lens groups 6, 7 coincide and thus are identical.

In the embodiment shown, the ratio between the absolute value of the focal length of the first lens group 6 and the absolute value of the focal length of the second lens group 7 is 0.85:1. The absolute value of the first lens group's 6 focal length is 23% of the absolute value of the overall focal length of the objective 5.

The first lens group 6 is disposed along the optical axis A between the focal plane 4 of the imaging system 2 and the second lens group 7. The second lens group 7 can be moved relative to the first lens group 6 along the optical axis A by actuator 70 for adjusting a working distance of the surgical microscope 1 between 200 mm and 5,000 mm. For this purpose the actuator 70 is coupled to a controller 10.

The invention is, however, not limited to the second lens group of the objective being moveable relative to the first lens group of the objective along the optical axis. Alternatively or additionally, also the first lens group, which is located along the optical axis between the focal plane of the imaging system and the second lens group, may be moveable along the optical axis relative to the second lens group for adjusting the working distance of the surgical microscope.

The two lens groups 6, 7 altogether image the focal plane 4 to infinity.

Between the objective 5 and the zoom system 8, each optical imaging path 2a, 2b respectively comprises a variable aperture stop 13, 13' for enabling an adjustment of intensity and depth of focus.

The four parts of the zoom system 8 each are cemented elements. Each cemented element is formed by two optical lenses of eight optical lenses 81 and 82, 83 and 84, 85 and 86, 87 and 88, 81' and 82', 83' and 84', 85' and 86', 87' and 88' of the zoom system, with the respective two lenses being glued face-to-face together and being made from materials with different refractive indices. The cemented elements are each consecutively passed through (traversed) by only one of the two stereoscopic optical imaging paths.

The lenses 83, 84 and 83', 84', respectively and 85, 86 and 85', 86', respectively, of the two central parts can each be moved by a drive 80, 80' relative to the lenses 81, 82 and 81', 82', respectively, and 87, 88 and 87', 88', respectively, for changing the magnification provided by the zoom system 8 between 8× and 20×.

Along the optical imaging paths 2a, 2b the imaging system 2 generates magnified images of the operation area 3 on reception areas 91, 91' of two CCD-sensors 9, 9'. The images of the operation area 3 received on the reception areas 91, 91' represent views of the operating area 3 at two slightly different angles. In the embodiment shown, the reception areas 91, 91' comprise a Bayer matrix providing a resolution of 1280× 1024 image elements. Based on electrical signals output from the reception areas 91, 91', the CCD-sensors 9, 9' construct two-dimensional single images of the operation area 3 imaged by the imaging system 2 which are output by the controller 10 to the at least one display 11. Although a total of four displays 11, 11', 11", and 11'" is shown in FIG. 1, only one display 11 is shown in FIG. 2 for the sake of clarity. Since the CCD-sensors 9, 9' output two images that are stereoscopically related to each other, a 3D-monitor is actually used as display 11.

The controller 10, which is a processor configured by software, is coupled to the CCD-sensors 9, 9', the drives 80, 80' of the zoom system 8, the drive 70 of the objective 5, the variable aperture stops 13, 13', and the at least one display 11 by data lines shown as dashed lines. The data line between the controller 10 and the aperture stops 13, 13' is not shown in FIG. 2 for sake of clarity.

A zero-degree illumination of the focus plane 4 is achieved with a light source 12 disposed along the optical axis of the objective 5. Since the radiation emitted from the light source 12 is passed through the lenses of the objective 5, the size of the illuminated portion of the focal plane 4 adjusts automatically to the size of the portion of the focal plane 4 that is actually imaged by the surgical microscope 1.

The controller 10 controls the drive 70 of the objective 5 continuously such that the imaged operation area 3 is always located within the focal plane 4 of the imaging system 2, and the imaging system 2 always provides a sharp image of the imaged operation area 3. The controller 7 further ensures by automatic mirroring and/or rotation of the single images that the operation area 3 is shown on the at least one display 11 in its correct position.

By varying the working distance between 200 mm and 1,200 mm, the surgical microscope can thus either be used as a surgical microscope or as an overview camera. A stereoscopic image with high magnification is provided at a short working distance AA of between 200 mm and 500 mm, while a larger portion of the focal plane is imaged with large working distances AA of between 1,000 mm and 1,200 mm.

Figure 3:
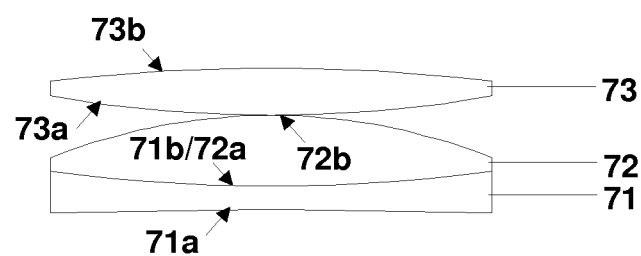
FIG. 3 shows a magnified schematic representation of the optical lenses of the objective of the surgical microscope of FIG. 2.
Figure 3:
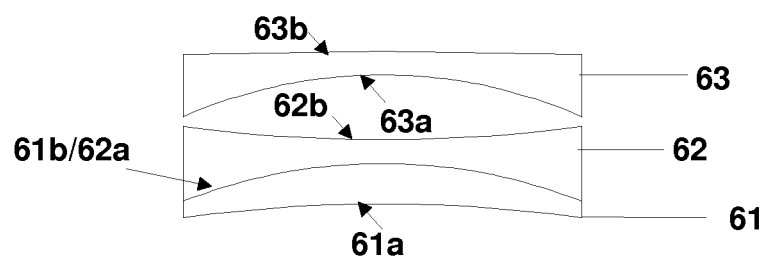

FIG. 3 shows a magnified representation of optical lenses 61, 62, 63, 71, 72, 73 of the objective 5 with the optical surfaces indicated by reference numerals.

The optical parameters of these optical lenses 61, 62, 63, 71, 72, 73 are as follows:

| Lens | Surface | Radius [mm] | Distance [mm] | Diameter [mm] | Medium | Refractive Index at 546 nm | Abbe Number |
|---|---|---|---|---|---|---|---|
| | | | | OBJECT | | | |
| | | | 200 . . . 5,000 | | Air | | |
| 61 | 61a | −146.3 | 3.5 | 36 | SF8 | 1.6942 | 30.94 |
| 61/62 | 61b/62a | −51.7 | 2 | 36 | BK3 | 1.5001 | 64.9 |
| 62 | 62b | 146.3 | 5.5 | 36 | Air | | |
| 63 | 63a | −48 | 2 | 36 | CAF2 | 1.435 | 94.7 |
| 63 | 63b | −520 | 24 . . . 4 | 36 | Air | | |
| 71 | 71a | −600 | 2 | 40 | SF8 | 1.6942 | 30.94 |

-continued

| Lens | Surface | Radius [mm] | Distance [mm] | Diameter [mm] | Medium | Refractive Index at 546 nm | Abbe Number |
|---|---|---|---|---|---|---|---|
| 71/72 | 71b/72a | 157 | 6 | 40 | CAF2 | 1.435 | 94.7 |
| 72 | 72b | −57.3 | 0.01 | 40 | Air | | |
| 73 | 73a | 120 | 4 | 40 | CAF2 | 1.435 | 94.7 |
| 73 | 73b | −182 | 1 . . . 21 | 40 IMAGE | Air | | |

The distance specified in a row of the table indicates the distance between the surface specified in said table row and the surface specified in the next row of the table. A medium specified in a table row accordingly indicates the material present between the surface specified in said row of the table and the surface specified in the next row of the table.

Since the second lens group 7 is moved as a whole, the values 24 . . . 4 and 1 . . . 21 change precisely diametrically opposed and to the same extent. Depending on the position of the second lens group 7, a free working distance of between 200 mm and 5,000 mm is achieved.

In the table, SF8, BK3, and CAF2 represent notations under which the respective dense flint glass, borosilcate glass, and calcium fluoride glass can be obtained from Schott AG in Germany.

For the objective shown in FIG. 3, the absolute value of the ratio of the focal length of the first lens group 6 of the objective 5 to the focal length of the second lens group 7 of the objective 5 is 0.85. Further, the absolute value of the ratio of the focal length of the first lens group 6 of the objective 5 to the minimum focal length of the objective 5 is 0.23.

It is noted that the present invention is not limited to the above embodiment and the optical lenses used therein.

Although the invention has been described above with respect to an example using a digital surgical microscope having no eyepieces, the present invention is not limited hereupon. Accordingly, each optical imaging path of the imaging system may have a lens barrel and an eyepiece in addition or alternatively to the CCD-sensors. An image reversal is hereby effected in the lens barrel for enabling a viewing of the correctly positioned operating area.

Although two separate CCD-sensors are used above for the stereoscopic optical imaging paths, also only one CCD-sensor with a respectively large reception area may alternatively be used for both optical imaging paths together.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

The invention claimed is:

1. A surgical microscope, comprising:
an imaging system that provides a magnified multidimensional image of an object disposable in a focal plane of the imaging system along at least one optical imaging path, the imaging system comprising an objective, the objective comprising at least two lens groups through which the at least one optical imaging path passes one after another, and which define the focal plane of the imaging system,
wherein at least one lens group of the objective is moveable along its optical axis relative to the at least one other lens group of the objective,
wherein the objective's first lens group which is located directly adjacent to the focal plane along the at least one optical imaging path consists of at least three optical lenses and has altogether a negative optical power, and
wherein the absolute value of the focal length of the first lens group of the objective does altogether not exceed 35% of the absolute value of a minimum focal length of the objective.

2. The surgical microscope according to claim 1, wherein the absolute value of the focal length of the first lens group of the objective does altogether not exceed 25% or 20% of the absolute value of the minimum focal length of the objective.

3. The surgical microscope according to claim 1, wherein the absolute value of the focal length of each single optical lens of the first lens group of the objective is between 80% and 300% or between 95% and 200% of the absolute value of the focal length of the first lens group of the objective.

4. The surgical microscope according to claim 1, wherein the first lens group of the objective consists of just three optical lenses, of which two optical lenses are joined together permanently to form a cemented element, and the third optical lens is a lens element separate from the cemented element.

5. The surgical microscope according to claim 1, wherein the objective's second lens group which is located along the at least one optical imaging path directly adjacent to the first lens group has altogether a positive optical power; and
wherein the second lens group of the objective consists of exactly three optical lenses, of which two optical lenses are joined together permanently to form a cemented element, and the third optical lens is a lens element separate from the cemented element.

6. The surgical microscope according to claim 1, wherein the optical lenses of each lens group are consecutively passed through by the same at least one optical imaging path, and are stationary relative to each other.

7. The surgical microscope according to claim 1, wherein no imaging of the focal plane to infinity takes place within each lens group.

8. The surgical microscope according to claim 1, wherein the objective as a whole effects an imaging of the object disposable in the focal plane of the imaging system to infinity.

9. The surgical microscope according to claim 1, wherein no imaging of the object disposable in the focal plane of the imaging system to infinity takes place within the objective.

10. The surgical microscope according to claim 1,
wherein the imaging system provides at least one pair of optical imaging paths intersecting at the focal plane of the imaging system at a stereoscopic angle of between 3 and 14, and provides a magnified multidimensional image of the object disposable in the focal plane of the imaging system; and
wherein the optical lenses of the objective are collectively passed through by the at least one pair of optical imaging paths.

11. The surgical microscope according to claim 10, wherein the imaging system, further comprises a zoom system having several optical lenses, with the optical lenses of the zoom system being consecutively passed through by just one optical imaging path of the at least one pair of optical imaging paths.

12. The surgical microscope according to claim 1, further comprising at least one image sensor disposed in an image plane of the imaging system and outputting image data representing the image of the object generated by the imaging system.

13. A surgical microscope comprising:
an imaging system that provides a magnified multidimensional image of an object disposable in a focal plane of the imaging system along at least one optical imaging path, the imaging system comprising an objective, the objective comprising exactly two lens groups through which the at least one optical imaging path passes, and which define the focal plane of the imaging system,
wherein at least one lens group of the objective is moveable along its optical axis relative to the at least one other lens group of the objective,
wherein the objective's first lens group which is located directly adjacent to the focal plane along the at least one optical imaging path consists of at least three optical lenses and has altogether a negative optical power,
wherein the absolute value of the focal length of the first lens group of the objective does altogether not exceed 35% of the absolute value of a minimum focal length of the objective, and
wherein a ratio of the absolute value of the focal length of the first lens group of the objective to the absolute value of the focal length of the second lens group of the objective is between 0.75 and 1.00 or between 0.80 and 0.90 or between 0.82 and 0.88.

14. The surgical microscope according to claim 13, wherein the absolute value of the focal length of each single optical lens of the first lens group of the objective is between 80% and 300% or between 95% and 200% of the absolute value of the focal length of the first lens group of the objective.

15. The surgical microscope according to claim 13,
wherein the first lens group of the objective consists of just three optical lenses, of which two optical lenses are joined together permanently to form a cemented element, and the third optical lens is a lens element separate from the cemented element;
wherein the objective's second lens group which is located along the at least one optical imaging path directly adjacent to the first lens group has altogether a positive optical power; and
wherein the second lens group of the objective consists of exactly three optical lenses, of which two optical lenses are joined together permanently to form a cemented element, and the third optical lens is a lens element separate from the cemented element.

16. The surgical microscope according to claim 13,
wherein the optical lenses of each lens group are consecutively passed through by the same at least one optical imaging path, and are stationary relative to each other; and
wherein no imaging of the focal plane to infinity takes place within each lens group.

17. The surgical microscope according to claim 13,
wherein the objective as a whole effects an imaging of the object disposable in the focal plane of the imaging system to infinity; and
wherein no imaging of the object disposable in the focal plane of the imaging system to infinity takes place within the objective.

18. A surgical microscope, comprising:
an imaging system that provides a magnified multidimensional image of an object disposable in a focal plane of the imaging system along at least one optical imaging path, the imaging system comprising an objective, the objective comprising at least two lens groups through which the at least one optical imaging path passes, and which define the focal plane of the imaging system,
wherein at least one lens group of the objective is moveable along its optical axis relative to the at least one other lens group of the objective,
wherein the objective's first lens group which is located directly adjacent to the focal plane along the at least one optical imaging path consists of at least three optical lenses and has altogether a negative optical power,
wherein the absolute value of the focal length of the first lens group of the objective does altogether not exceed 35% of the absolute value of a minimum focal length of the objective,
wherein the optical lenses of each lens group are consecutively passed through by the same at least one optical imaging path, and are stationary relative to each other; and
wherein no imaging of the focal plane to infinity takes place within each lens group.

19. The surgical microscope according to claim 18, wherein the absolute value of the focal length of each single optical lens of the first lens group of the objective is between 80% and 300% of the absolute value of the focal length of the first lens group of the objective.

20. The surgical microscope according to claim 18,
wherein the first lens group of the objective consists of just three optical lenses, of which two optical lenses are joined together permanently to form a cemented element, and the third optical lens is a lens element separate from the cemented element;
wherein the objective's second lens group which is located along the at least one optical imaging path directly adjacent to the first lens group has altogether a positive optical power; and
wherein the second lens group of the objective consists of exactly three optical lenses, of which two optical lenses are joined together permanently to form a cemented element, and the third optical lens is a lens element separate from the cemented element.

21. The surgical microscope according to claim 18,
wherein the objective as a whole effects an imaging of the object disposable in the focal plane of the imaging system to infinity; and
wherein no imaging of the object disposable in the focal plane of the imaging system to infinity takes place within the objective.

* * * * *

UNITED STATES PATENT AND TRADEMARK OFFICE
CERTIFICATE OF CORRECTION

PATENT NO.       : 9,046,688 B2
APPLICATION NO.  : 14/272866
DATED            : June 2, 2015
INVENTOR(S)      : Artur Hoegele Page 1 of 1

It is certified that error appears in the above-identified patent and that said Letters Patent is hereby corrected as shown below:

On the Title Page, item (72) Inventors: delete "(US)" and insert --(DE)--, therefor.

In the claims,

In Column 10, line 59, delete "3" and insert --3°--, therefor.

In Column 10, line 60, delete "14" and insert --14°--, therefor.

Signed and Sealed this
Twenty-fourth Day of November, 2015

Michelle K. Lee
*Director of the United States Patent and Trademark Office*